United States Patent
Sage, Jr. et al.

(10) Patent No.: US 7,361,155 B2
(45) Date of Patent: Apr. 22, 2008

(54) COMPENSATING LIQUID DELIVERY SYSTEM AND METHOD

(75) Inventors: Burton H. Sage, Jr., Vista, CA (US); David Gillett, San Diego, CA (US); Brian Catanzaro, San Diego, CA (US)

(73) Assignee: TheraFuse, Inc., Carlsbad, CA (US)

( * ) Notice: Subject to any disclaimer, the term of this patent is extended or adjusted under 35 U.S.C. 154(b) by 397 days.

(21) Appl. No.: 10/662,871

(22) Filed: Sep. 16, 2003

(65) Prior Publication Data

US 2005/0059926 A1    Mar. 17, 2005

(51) Int. Cl.
*A61M 31/00* (2006.01)

(52) U.S. Cl. .......................... 604/65; 700/282

(58) Field of Classification Search ............ 604/65–67, 604/246, 537; 700/282
See application file for complete search history.

(56) References Cited

U.S. PATENT DOCUMENTS

| | | |
|---|---|---|
| 3,469,578 A | 9/1969 | Bierman |
| 3,552,855 A | 1/1971 | Crosswy et al. |
| 4,318,400 A | 3/1982 | Peery |
| 4,340,083 A | 7/1982 | Cummins |
| 4,447,224 A | 5/1984 | Idriss et al. |
| 4,447,232 A | 5/1984 | Sealfon |
| 4,468,221 A | 8/1984 | Mayfield |
| 4,532,811 A | 8/1985 | Miller, Jr. et al. |
| 4,741,736 A | 5/1988 | Brown |
| 4,777,368 A | 10/1988 | Kerlin, Jr. |
| 4,857,048 A | 8/1989 | Simons et al. |
| 4,874,386 A | 10/1989 | O'Boyle |
| 4,886,499 A | 12/1989 | Cirelli |
| 4,938,079 A | 7/1990 | Goldberg |
| 4,938,368 A | 7/1990 | Sharman |
| 4,979,940 A | 12/1990 | Bobo, Jr. et al. |
| 5,016,047 A | 5/1991 | Meacham |
| 5,061,242 A | 10/1991 | Sampson |
| 5,163,920 A | 11/1992 | Olive |
| 5,211,626 A | 5/1993 | Frank et al. |
| 5,248,300 A | 9/1993 | Bryant et al. |
| 5,527,288 A | 6/1996 | Gross et al. |
| 5,533,412 A | 7/1996 | Jerman et al. |
| 5,575,770 A | 11/1996 | Melsky et al. |
| 5,665,070 A | 9/1997 | McPhee |
| 5,685,844 A * | 11/1997 | Marttila ........................ 604/65 |
| 5,848,990 A | 12/1998 | Cirelli et al. |
| 5,984,894 A * | 11/1999 | Poulsen et al. .............. 604/151 |

(Continued)

FOREIGN PATENT DOCUMENTS

EP    1 177 802    6/2002

*Primary Examiner*—Nicholas Lucchesi
*Assistant Examiner*—Theodore J Stigell
(74) *Attorney, Agent, or Firm*—Foley & Lardner LLP (57) ABSTRACT

A device and method for accurate delivery of a liquid is described. The device comprises a flow channel through which the liquid flows. During manufacture or at some other point prior to the delivery of the liquid, the flow channel is characterized in terms of one or more properties of flow of a liquid through the channel. This characterization is stored in such a way that the flow channel characterization is available to the liquid delivery device at time of use. At time of use, the liquid delivery system reads the stored flow channel characterization and uses the stored flow channel characterization for safe and accurate delivery of the liquid.

34 Claims, 6 Drawing Sheets

U.S. PATENT DOCUMENTS

| | | |
|---|---|---|
| 6,074,369 A | 6/2000 | Connelly et al. |
| 6,162,202 A | 12/2000 | Sicurelli et al. |
| 6,386,050 B1 | 5/2002 | Yin et al. |
| 6,582,393 B2 * | 6/2003 | Sage, Jr. ................... 604/65 |
| 6,589,229 B1 * | 7/2003 | Connelly et al. ........ 604/890.1 |
| 6,709,313 B2 | 3/2004 | Kondo et al. |
| 6,932,796 B2 | 8/2005 | Sage et al. |
| 2005/0005710 A1 | 1/2005 | Sage et al. |
| 2005/0050941 A1 | 3/2005 | Sage et al. |

* cited by examiner

COMPENSATING LIQUID DELIVERY SYSTEM AND METHOD

FIELD OF THE INVENTION

This invention relates generally to liquid delivery systems and more particularly to compensating infusion systems.

BACKGROUND OF THE INVENTION

Accurate delivery of liquids, particularly in the field of infusion of medical liquids, and especially in the field of IV infusion of pharmaceuticals, is becoming more and more critical as the potency of infusible therapeutic agents continues to increase. Historically, IV infusions were performed with the active ingredient dissolved in an appropriate vehicle hanging in a bag from a pole above the patient. Such gravity bag infusion, while able to provide the medical liquid to the patient in a continuous fashion, suffered from accuracy problems. Because the driving force is derived from the distance the solution in the bag is above the infusion site, the driving force would change with any change in distance, such as when the bag empties of solution, when the patient moved from a prone position to lying on a side, and especially when the patient arose from bed.

The rate of infusion would also change with temperature due to changes in the viscosity of the medical liquid, and could drastically change when different medical liquids were used. Further, the rate of infusion would change significantly when different infusion sets were used due to the manufacturing tolerances of the inside diameter of the flow tube. While the user of a gravity bag infusion set could adjust the infusion rate using a roller clamp on the tube and counting the drips per second in a drip chamber included in the infusion set, the accuracy of such an adjustment was qualitative at best.

To overcome these limitations, positive displacement pumps have replaced gravity bags for the infusion of medical liquids, especially for those liquids where precise control of the delivery rate is important. These positive displacement pumps include syringe pumps, where the volume of fluid to be infused is relatively small and peristaltic pumps where the volume of the medical liquid to be infused is relatively large. Positive displacement pumps are designed in such a way that a fixed volume of liquid is delivered independent of the pressure required to deliver the liquid or the viscosity of the delivered liquid. With these two variables removed, infusion pumps overcame two of the major obstacles to accurate delivery which are inherent in gravity bag infusion systems.

These positive displacement medical liquid infusion systems are "open-loop" systems in that they rely on the dimensional accuracy of system components to achieve accurate delivery. For syringe pumps, for example, the accuracy of delivery is mainly dependent on the inside diameter of the barrel of the syringe in use. Since the accuracy depends on the square of the inside diameter, it is important to manufacture these syringes with close tolerances. For peristaltic pumps, the accuracy of delivery depends on the inside diameter of the flow tube at the site where the peristaltic pumping occurs. Again, the delivery accuracy depends on the inside diameter of the flow tube to the second power, so manufacturing tolerances are relatively tight.

If system components are used that are outside of the specification range, such positive displacement systems will inaccurately deliver the medical liquid. In such an instance, there is no provision to correct or compensate for the out of range dimension. In an attempt to address this problem, closed loop medical liquid infusion systems have been described (see, e.g., Frank U.S. Pat. No. 5,211,626). This system measures the flow rate of the medical liquid along the flow channel and then adjusts the position of a proportional valve to achieve the desired flow rate. This closed loop system, however, fails to distinguish between changes in flow rate due to temperature, viscosity, or flow channel dimensions. Because the flow rate has differing exponential dependence for these flow rate variables, the calculated valve adjustment is usually incorrect, resulting in inaccurate infusion of the medical liquid.

Despite the transition from simple and inexpensive gravity bags, the complicated and expensive infusion pumps typically fail to achieve highly accurate delivery or to provide evidence that the desired drug delivery is occurring or has occurred (other than that the motor is operating or has operated). The actual flow rate remains unverified and uncompensated.

SUMMARY OF THE INVENTION

In accordance with one embodiment, a device for delivering liquid via a flow channel is disclosed. The device includes a memory having a stored value indicative of a flow characteristic of the flow channel, a controller that generates a flow control signal based on the stored value, and a valve responsive to the flow control signal for controlling flow of the liquid.

In accordance with another embodiment, a method of manufacturing a liquid delivery device is disclosed. The method includes (i) coupling a portion of a flow channel of the device to a flow sensor of the device, providing a predetermined liquid for flow through the flow channel, measuring flow-related data of the flow of the predetermined liquid through the flow channel using the flow sensor, and calculating a value of the flow characteristic of the flow channel based on the flow-related data, and storing the value in a memory of the liquid delivery device.

In accordance with yet another embodiment, a method is disclosed for delivering a liquid via a flow channel at a desired flow rate. Flow-related data of the liquid in the flow channel is measured, and a memory is accessed for a flow characteristic of the flow channel stored therein. A value of the flow rate of the liquid is calculated based on the flow-related data and the stored characteristic value, and the calculated value of the flow rate is compared to the desired flow rate. A valve is then controlled to achieve the desired flow rate.

DETAILED DESCRIPTION OF THE PREFERRED EMBODIMENTS

In accordance with the practice of one embodiment of the invention, a liquid delivery system is disclosed that provides accurate delivery of the liquid despite variability in one or more factors otherwise determinative of flow rate, such as by way of example and not by way of limitation, the dimensions of flow system components, driving force (e.g., pressure), and fluid viscosity. Compensating for such variables enables, for instance, cost-efficient, accurate delivery of infusible medical fluids from a gravity bag without the use of a positive displacement infusion pump. It is noted that practice of the present invention is not limited to the IV or continuous infusion context. One or more embodiments of the invention has applicability to the delivery of a broad range of medical fluid and non-medical fluid contexts in either a continuous or discontinuous (e.g., pulsed) manner. Moreover, one of the advantages of the degree to which the disclosed device and method provides compensated liquid delivery is the ability to use the same infusion device for accurate delivery of a number of liquids without the need to reconfigure, recalibrate or otherwise modify the device in preparation for use.

In accordance with one embodiment, a drug delivery device is disclosed for use with an infusion set that contains a flow channel having a flow characteristic that is predetermined via, for example, measurement during manufacture or during a calibration step. The drug delivery device has a memory in which the predetermined flow characteristic is stored prior to use or operation of the device. At time of operation or use, the infusion set is mated with a flow regulator capable of reading the stored flow characteristic and further capable of making similar measurements during use. A valve in the flow regulator is controlled based on the flow measurements and the stored flow characteristic to achieve a desired flow rate.

Figure 1:
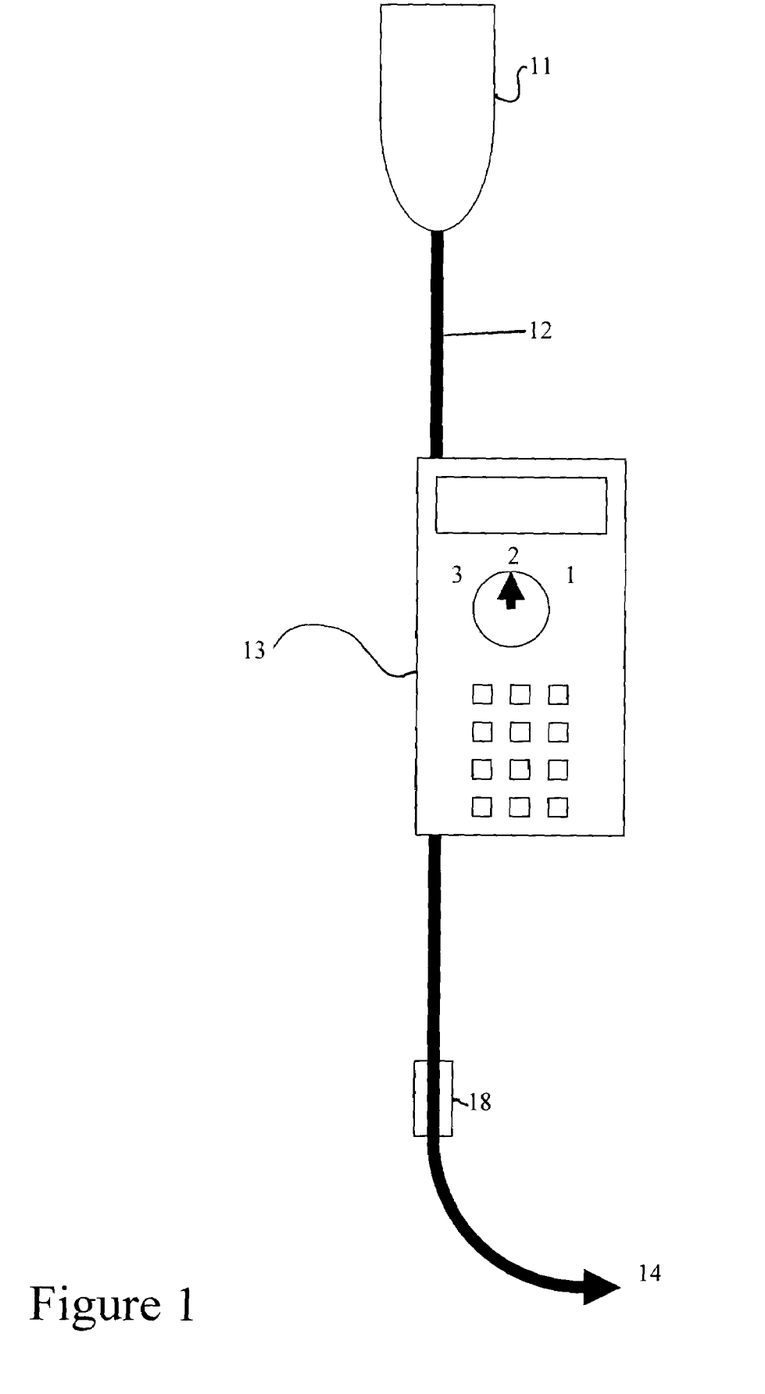
FIG. 1 is a schematic representation of a drug delivery system involving a patient receiving intravenous therapy from a gravity bag.
Figure 2:
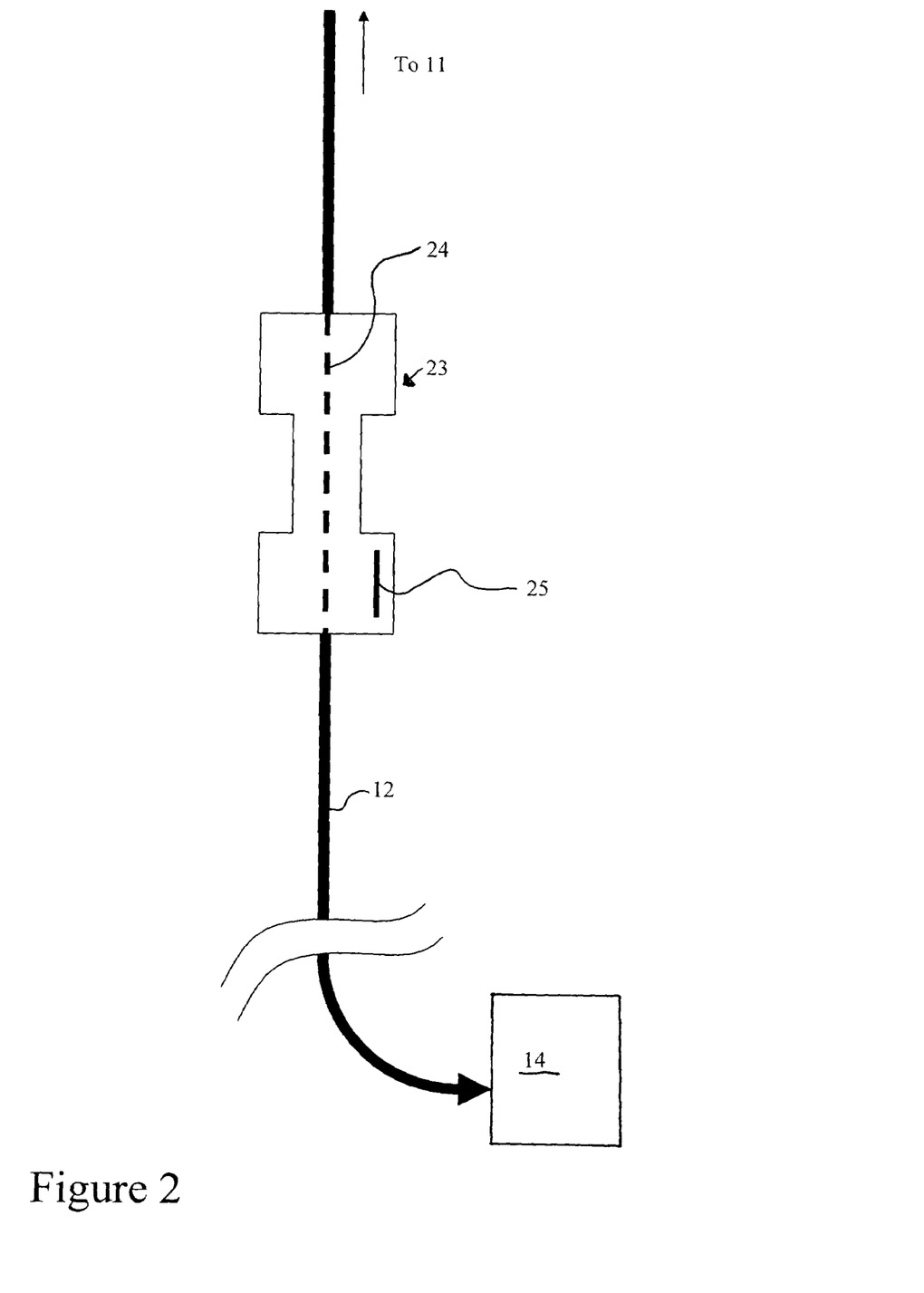
FIG. 2 is a schematic representation of an infusion set of the drug delivery system of FIG. 1 having a flow channel, the flow characteristic of which is used in connection with the teachings of one or more embodiments of the present invention.

Reference is made to FIGS. 1 and 2. Shown in FIG. 1 is a drug infusion system for providing intravenous therapy using a gravity bag 11 joined to an infusion set 12 and flowing through a flow regulator 13 to an infusion site 14 at the patient (not shown). Gravity bag 11 may contain any liquid or liquid formulation (e.g., a medicament) in an appropriate vehicle. The gravity bag in one embodiment of the present invention cab be put into service with an appropriate distance of the fluid above the patient's heart to insure acceptable fluid flow. The gravity bag 11 and infusion set 12 may be constructed as is well known in the art with materials used for fabrication in an IV infusion context, such as by way of example and not by limitation, silicones, polyvinyl chlorides and polyolefins.

FIG. 2 shows infusion set 12 in greater detail. Infusion set 12 may include a drip chamber (not shown) for visual evidence of fluid flow as is well known in the art. In one embodiment, infusion set 12 includes flow channel assembly 23. Flow channel assembly 23 comprises a flow channel 24 through which the medical liquid flows to the patient. Flow channel 24 also comprises read write memory 25 for storing a characteristic of liquid flow measured during manufacture or otherwise prior to operation.

Figure 3:
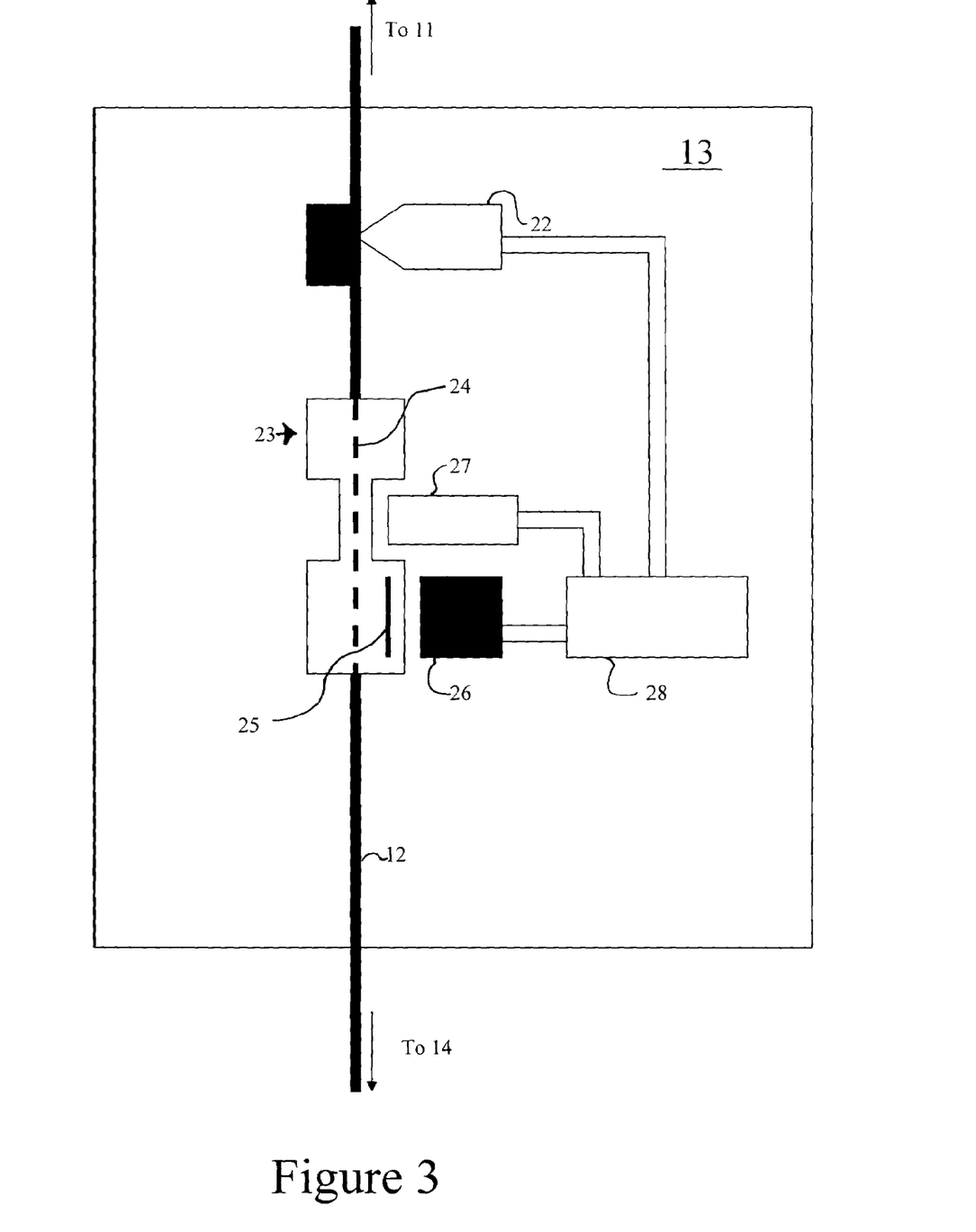
FIG. 3 is a schematic representation of a flow regulator of the drug delivery system of FIG. 1 where the flow regulator is mated with a flow cell inserted into the infusion line in accordance with the teachings of one embodiment of the present invention.

With reference now to FIG. 3, flow regulator 13 is shown mated to infusion set 12 at the location on infusion set 12 where flow channel assembly 23 is located. This mating can be, in some embodiments, made with a latching mechanism, which may be mechanical or magnetic as is well known in the art, so that the various components of flow regulator 13 and flow channel 23 are held in place once the mating has occurred. Once properly mated, some embodiments of flow regulator 13 are capable of making measurements of properties of flow in flow channel 24. Some examples of methods of making measurements of properties of flow are described in co-pending and commonly assigned application Ser. No. 10/600,296 (entitled "Compensating Drug Delivery System"), the contents of which is incorporated by reference in its entirety.

Access to the patient's body at infusion site 14 is made with a body access device (not shown) which may by way of example and not by limitation, be a traditional stainless steel needle or may soft-set catheters placed with a catheter inserter or may be an array of microneedles.

FIG. 3 shows in greater detail the portion of infusion set 12 where flow channel assembly 23 mates with flow regulator 13. In one embodiment, flow channel assembly 23 is recessed to receive a flow sensor 27 such that it accurately registers with flow sensor 27. Such recesses may be conical in shape, or rectangular with slanted sides, as is well known in the art, so that once mated, optical components (not shown) in flow sensor 27 are aligned with flow channel 24 to make measurements of flow and held in that alignment.

In use, flow sensor 27 makes measurements of properties of flow along flow channel 24. Such properties include, but are not limited to volumetric flow rate, the velocity of the fluid flow, and the time required for an increment of volume to flow a prescribed distance along the flow channel (time of flight). Some methods and devices for measuring time of flight of fluids are described in detail in the above-identified application.

Flow channel 24 also is coupled to read/write memory 25 as shown in FIGS. 2 and 3. In accordance with one embodiment, during manufacture of flow channel 24, a flow sensor essentially identical to flow sensor 27 was used to measure flow properties of a standardized fluid in flow channel 24. In one method of manufacture, the following steps would be used.

1) Flow channel 24 would be fabricated.

2) Read/write memory device 25 would be fabricated.

3) Flow channel 24 and read/write memory device 25 would be assembled into flow channel assembly 23.

4) Flow channel assembly 23 would be mounted in a flow measurement fixture (not shown) and flow properties of flow channel 24 would be measured.

5) The measured flow properties of flow channel 24 would then be stored in read/write memory device 25. Some examples of read/write memories are an RFID (radio frequency identification) chip and a bar code, although other forms of read/write memories may be used. An RFID chip or a bar code might permit the flow properties to be read at time of use without making electrical contact with flow channel assembly 23.

6) Flow channel assembly 23 would be removed from the flow measurement fixture.

7) Flow channel assembly 23 would be cleaned and dried and assembled into infusion set 12.

At time of use, read/write memory reader 26 of flow regulator 13 reads the flow properties in read/write memory 25. In use, flow sensor 27 makes measurements of some or all of the same flow properties measured during manufacture of the medicament to be delivered. Using the flow measurements of the standardized fluid from read/write memory 25, and the flow measurements of the medicament to be delivered, the actual flow rate can be matched to the flow rate desired by the user, achieving highly accurate delivery of the medicament to the patient in accordance with the calculations set forth herein.

Figure 4:
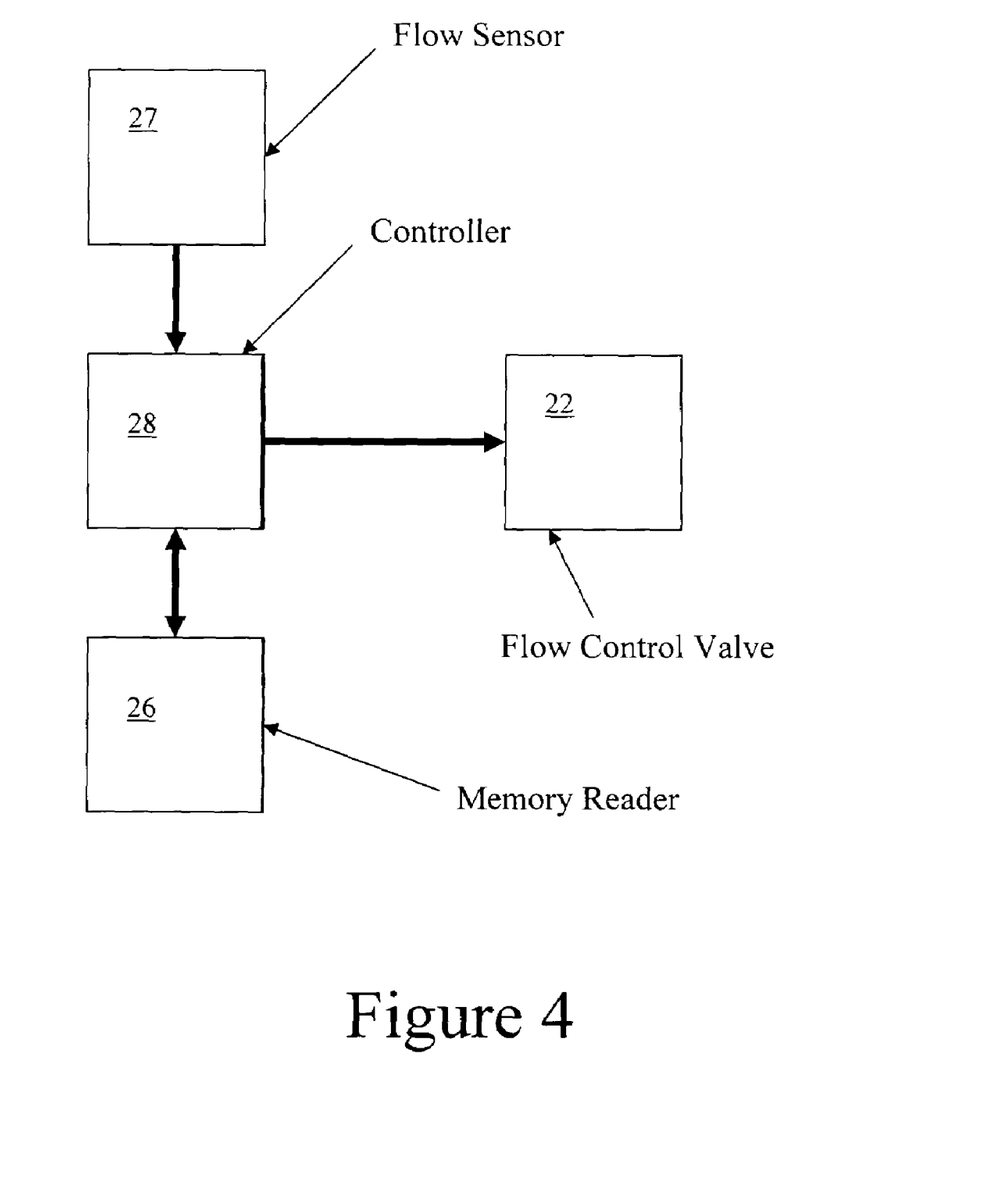
FIG. 4 is a schematic representation of a liquid delivery device in accordance with one embodiment of the present invention.

The flow or processing of information in the compensating drug delivery device is shown in FIG. 4. Once flow regulator 13 is mated to infusion set 12, read/write memory reader 26 of flow regulator 13 reads the stored flow characteristics in memory 25 of infusion set 12. During use or operation, when a medical liquid is flowing from gravity bag 11 to the patient at infusion site 14, flow sensor 27 makes measurements of the same flow characteristic and provides the flow characteristic information or data to controller 28. Controller 28 determines, by way of example and not by limitation, through the use of calculations or a look up table, information regarding flow of the medical liquid based on the characteristic stored in memory 25 and the measurement of the characteristic made by flow sensor 27 during use. Using these calculations, controller 28 controls flow control valve 22 to achieve the require flow of the medical liquid to the patient.

The calculations made by controller 28 can be made in the context of the following principles. In other embodiments of the present invention, some or all of the results of the calculations can be achieved through the use of look up tables. For fluids in laminar flow in a channel with a circular cross section, the volumetric flow rate Q is given by the Poiseuille's equation:

$$Q = \frac{\Pi P A^2}{8 \eta L} \quad (1)$$

Where
Q=flow rate in volume per time
P=Pressure
A=flow channel effective cross sectional area
$\eta$=fluid viscosity
L=flow channel length Flow rate Q is also given by AV where again A is the effective cross sectional area of the circular flow tube and V is the average velocity of flow of the fluid down the channel. Please note the use of the words effective and average. This usage is due to the fact that no flow channel is perfectly round or has exactly the same cross sectional area at all points along the flow channel. Because of this variation in cross sectional area, the velocity of the liquid will not be exactly the same at all points along the channel. Note further that A can be expressed in terms of an effective radius R such that $A=\pi R^2$ or in terms of an effective diameter D such that $A=\pi D^2/4$.

The velocity of flow in a channel can be approximated by the "Thermal Time of Flight" method, described in U.S. Pat. No. 6,582,393, the contents of which are incorporated herein by reference in its entirety. In general, the fluid is heated at one point along the channel, and the heated fluid is detected downstream by a heat sensor. The velocity is calculated by measuring the distance downstream from the point of heating to the point of detection and dividing that distance by the elapsed time between heating the fluid and detecting the heated fluid. Letting X equal the separation distance between the point of heating and the point of detection, and T equal the measured time of flight, the flow rate Q=AX/T.

In a drug delivery system where a reusable flow regulator is mated with a flow channel on a disposable infusion set, the flow regulator might be used with a plurality of unknown flow channels. Given routine manufacturing tolerances of flow channels, their cross sectional area may vary as much as 25%. Further, by way of example and not by limitation, when the source of medicament is a gravity bag, the height of the liquid above the infusion site may vary as well as the height of the liquid surface in the bag. Thus the driving pressure from the elevated fluid will vary. Further still, an intravenous infusion system should provide accurate delivery of many different medicaments which have a wide viscosity range. Thus, some or all of the variables that determine the actual flow rate, such as by way of example: flow channel cross section area, pressure, and viscosity, are all generally unknown. The final variable, the length of the flow tube, can be accurately set during manufacture, and will not be considered further here. (However, the present invention can be used to address variations in tube length as well.)

To address this problem, the following method may be used. In the laboratory, a nominal or standard flow system that is identical or substantially identical to the planned production system except for manufacturing tolerances of the flow tube cross section area is set up. Using the standard AAMI (Association for the Advancement of Medical Instrumentation) protocol, the flow rate through this standard system is measured by weighing the amount of a standard fluid that has been delivered for a fixed period of time. The temperature of the liquid (to establish its viscosity), and the driving pressure are also set at nominal or standard values. A flow tube is also selected to be a reference standard.

Letting the subscript o denote the nominal, standard or predetermined flow condition, Poiseuille's equation for the nominal or standard setup is given by:

$$Q_0 = \frac{\Pi P_0 A_0^2}{8 \eta_0 L} \quad (2)$$

For a randomly selected flow channel measured under these conditions, wherein the subscript 1 is used to denote a randomly selected flow channel, the flow rate is:

$$Q_1 = \frac{\Pi P_0 A_1^2}{8 \eta_0 L} \quad (3)$$

By dividing these two equations, the following useful result is obtained:

$$Q_1/Q_0 = A_1^2/A_0^2 \quad (4)$$

And, using the relationship Q=AX/T, which can be used since pressure and viscosity have been set at standard conditions, it can be shown that $$T_0/T_1 = A_1/A_0 \quad (5)$$

Thus the flow rate for the randomly selected tube can be determined as $$Q_1 = Q_0 T_0^2 / T_1^2 \quad (6)$$

The above equation gives the flow rate in the randomly selected tube in terms of the flow rate in the nominal or standard tube, the measured time of flight in the standard tube, and the measured time of flight in the randomly selected tube given the nominal or standard pressure and the nominal liquid at nominal temperature.

Figure 6:
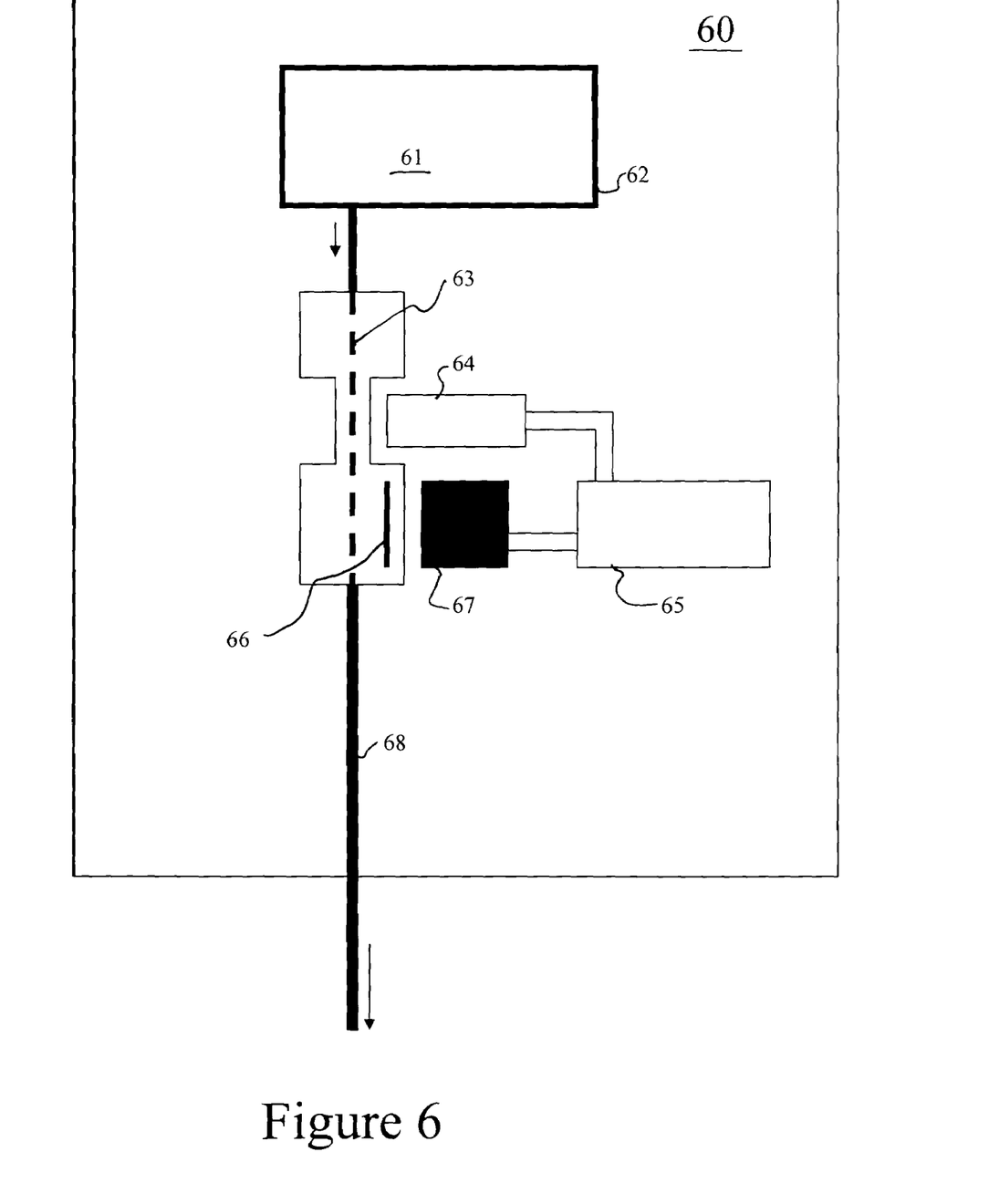
FIG. 6 is a schematic representation of a manufacturing fixture of the flow channel of FIG. 1 where the flow characteristic of the flow channel is measured in accordance with the teachings of the present invention.

A manufacturing fixture 60 that may be used to measure $T_1$ is shown in FIG. 6. Standard fluid 61 is shown in pressurized container 62. Temperature $T_0$ is established for the standard fluid flowing through the flow channel being measured 63 and pressure $P_0$ is established for causing the standard fluid to flow through the flow channel 63. Flow channel 63 is temporarily mated with flow sensor 64 and standard fluid 61 caused to flow through channel 63 and finally to waste through waste pipe 68. When standard fluid 61 is flowing through flow channel 63, time of flight $T_1$ is measured. A manufacturing fixture with many essentially identical flow sensors and the same number of mating sites for flow channels could be created such that $T_1$ for many flow channels could be measured at the same time. Processor 65 calculates $Q_1$ using $T_1$, $Q_0$, and $T_0$ and loads all four factors into read/write memory 66 using read/write memory writer 67. Factors $Q_0$ and $T_0$ may also be carried as part of the programming in flow regulator 13. In some embodiments of the present invention, these measurements may be used, by way of example and not by limitation, for the purposes of quality control; rejecting flow channels where the measured time of flight and flow rate are outside established specification ranges. Read/write memory 66 may also contain inventory information such as date of manufacture, expiration date, lot number, and other such quality control information as may be necessary. This information would also be written into read/write memory 66 by read/write memory writer 67.

When infusion set 12 with flow channel 24 is mated with flow regulator 13 as shown in FIG. 3, read/write memory reader 26, which reads the information stored in read/write memory 25, reads $T_1$ and flow rate $Q_1$. As a practical matter, the acceptable specification ranges for $Q_1$ would be set higher than any expected delivery rate for the infusion system because flow control valve 22 can only be closed from its open position, not opened further so that partial closing of valve 22 achieves the desired flow rate.

In use with an unknown fluid at an unknown pressure, flow sensor 27 would measure an actual time of flight $T_a$. Using the equation Q=AX/T, the actual flow rate $Q_a$ can be calculated as $Q_a = Q_1 T_1 / T_a$ since the terms A and X are common.

In some embodiments for intravenous drug delivery, the compensating drug delivery system of the invention is then used in the following way as shown in FIG. 1. Using infusion set 12, gravity bag 11, and roller clamp 18, the infusion set is primed. Once the medication to be delivered appears at the output of infusion set 12, roller clamp 18 would be closed. Flow regulator 13, which has been set to the OFF condition (Position 1 in FIG. 1), is then mated to flow channel assembly 23 on the infusion set. The Set function of flow regulator 23 is then selected (position 2 of flow regulator 23 in FIG. 1). This setting causes flow control valve 22 to fully close. Roller clamp 18 is now opened. No flow from the end of infusion set 12 verifies that control valve 22 is closed. The user now sets the end of infusion set 12 in the vein of the patient at infusion site 14 (not shown) and selects the desired flow rate for the medication in gravity bag 11 using the keypad on flow regulator 13. Once the flow rate is selected, the user selects a Run mode (position 3 on flow regulator 13). Once in this Run mode, controller 28 of the flow regulator 13 generates a flow control signal to begin to open flow control valve 22 while directing the flow sensor 27 to make very frequent measurements of time of flight or other such flow parameter as may be appropriate. Since values of $Q_1$ and $T_1$ are stored and available via read/write memory 25 and read/write memory reader 26, and sensor 27 is measuring time of flight $T_a$, for every measurement of $T_a$, controller 28 can calculate the actual flow rate $Q_a$. Based on the actual flow rate, and assuming that the actual flow rate is not the flow rate selected by the user, controller 28 sends a signal to flow control valve 22 to open or close. Flow sensor 27 continues making time of flight measurements, and controller 28 continues to calculate the actual flow rate and adjusting flow control valve 22 until the actual flow rate $Q_a$ matches the selected flow rate within the accuracy limitations of the system. In this embodiment for intravenous delivery of a liquid medicine, once the calculated flow rate is within the required limits of the set flow rate, flow regulator 13 can enter a flow rate maintenance mode, reducing the frequency of measurements of the time of flight to conserve power.

In other embodiments of the present invention, a volume value can be used and thus stored in the memory. For example, a volume value can be determined by multiplying $Q_1$ and $T_1$ together. This could result, by way of example, in a memory that only needs to store one value.

In yet other embodiment of the present invention, an effective cross-sectional area, radius, or diameter of the flow channel can be used and stored in a memory to practice the present invention. In such an embodiment, the memory could store a velocity value which could be multiplied with the just mentioned effective dimensions and, if need be, other geometric values, to obtain a value that can be divided by the time of flight to obtain the value for the volume flow rate through the flow channel.

In the maintenance mode, any changes in temperature, which cause viscosity changes, or any changes in pressure, such as the patient elevating themselves in bed, will cause changes in the flow rate. Since flow regulator 13 is making time of flight measurements with flow sensor 27, the system will detect these changes and adjust flow control valve 22 by either opening the valve slightly, by way of example only, as in the case of lower pressure, or closing the valve slightly, such as, by way of example only, in the case of a higher temperature which reduces the viscosity of the solution, to maintain the selected flow rate. It should be understood from the foregoing that the valve 22 is in some embodiments a proportional or other valve that provides for suitable flow modifications. The valve described by Frank in U.S. Pat. No. 5,211,626 could be a suitable choice, the contents of U.S. Pat. No. 5,211,626 being incorporated by reference herein in its entirety.

The read/write memory 25 may be RFID chip MCRF 355/360 manufactured by Microchip Technology, Inc. of Chandler, Ariz. or any other memory capable of storing and providing data of the aforementioned type in typical read/write fashion. Controller 28 may be any standard microprocessor as is known in the art.

Practice of the present invention is not limited to the IV or continuous liquid flow context as described in the above embodiments. Sage, in U.S. Pat. No. 6,582,393 describes a device and method for measuring flow rate and compensating for flow system variables that accommodates the different exponential dependence of flow system variables on flow rate. In the device of Sage, a read/write memory could be included in the device, coupled to the flow channel as in the current invention, to provide the described geometric data. When used in such a system, the possible need to know properties of the medicament solution and the pressure under which the medicament solution is stored might be eliminated. Thus, in such a system, the reservoir could be pressurized at time of use rather than having to be manufactured at a pressure and having to have a reservoir that would maintain this pressure during storage.

Figure 5:
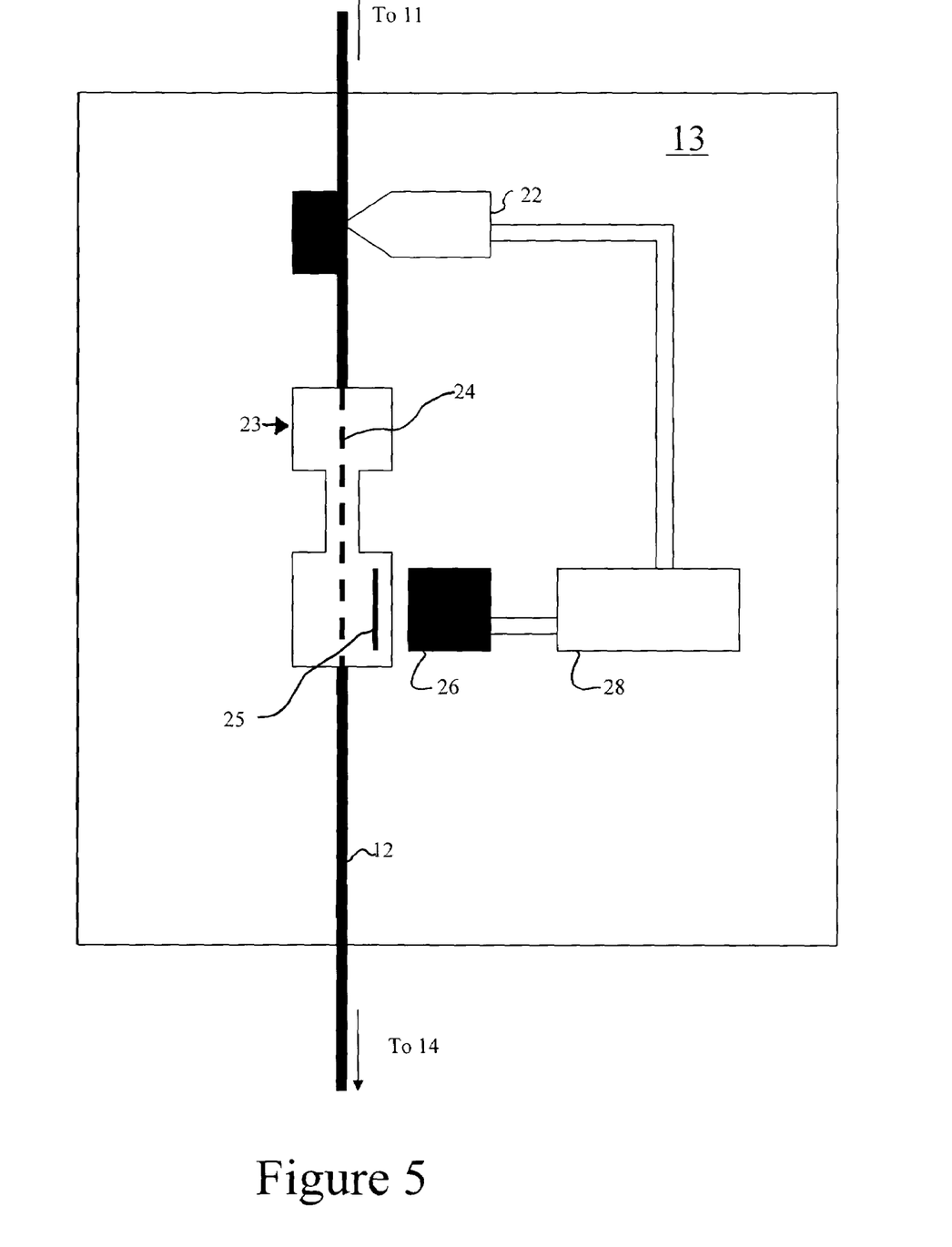
FIG. 5 is a schematic representation of a flow regulator of the drug delivery system of FIG. 1 where the flow regulator is mated with a flow cell inserted into the infusion line in accordance with the teachings of a second embodiment of the present invention.

Yet another embodiment is shown in FIG. 5. FIG. 5 shows valve assembly 22 controlling flow of the fluid through infusion set 12. Valve assembly 22 is controlled by controller 28 and receives flow characteristics of flow channel 24 from read/write memory 25 as read by read/write memory reader 26. The device of FIG. 5 is particularly useful when the liquid to be infused is known, such that its viscosity vs. temperature characteristic is known, and when this known drug is contained in a reservoir under mechanical pressure wherein the pressure profile as the reservoir empties is known. In such a case, flow rate sensor 27 as shown in FIG. 3 is not needed. When infusion set 12 is mated to flow regulator 13, read/write memory reader 26 reads the flow characteristic from read/write memory 25. Based on calculations performed by controller 28 using the theory developed above, especially equation (1) with a viscosity calculated given the reading from a temperature sensor (not shown) and the viscosity profile of the known drug, and with a pressure based on the amount of the known drug remaining in the reservoir as calculated from the delivery history for this reservoir, the actual flow rate may be closely predicted. This predicted flow rate may be compared to the desired flow rate selected by the user, and control valve 22 may be adjusted such that the predicted flow rate matches the desired flow rate within the accuracy limits of the device. Alternately, using the periodic method of achieving a desired flow rate as described by Sage in U.S. Pat. No. 6,582,393, the time that an on off valve is open or closed during a delivery cycle may be adjusted to achieve the desired dosing profile, which may be a constant flow rate or a flow rate profile stored in the device.

By way of example, this embodiment could be practiced by receiving data from a memory having a flow characteristic of the flow channel stored therein, providing viscosity information of the selected liquid, providing information related to the pressure causing the selected liquid to flow along the flow channel, determining a value of the flow rate of the selected liquid based on the stored flow characteristic, the viscosity information and the pressure information, comparing the determined flow rate to the desired flow rate, and controlling a valve to achieve the desired flow rate.

Regarding accuracy, it is believed that some embodiments of the present invention can enable a volumetric flow rate of a fluid passing through a flow channel to be determined to within 3% of its actual value, while refined embodiments can be practiced that will permit determination to within or substantially within 2%, 1%, 0.75%, 0.5%, 0.25% and 0.1 percent or even greater of its actual value. In other embodiments of the invention, the fluid flow can be controlled to these values as well.

In other embodiments of the present invention, highly volumetric flow rates can be determined with high accuracy, by way of example and not by limitation, to the rates just mentioned, without utilizing actual dimensions of the interior of the flow channel. For example, in some embodiments of the present invention, it will not be necessary to measure the actual inner diameter of the flow channel, or to determine the approximate inner diameter of the flow channel based on, for example, engineering design drawings, etc.

Some embodiments of the present invention utilize a fully automatic flow rate determination system. That is, by way of example and not by limitation, other than the need for a human to interface the infusion set with the flow regulator and to perform other ancillary steps, flow rate can be determined without human intervention. However, in other embodiments of the present invention, the present invention can be practiced with human assistance alone or in combination with an automated system.

The present invention also comprises software and firmware that is written/created to practice any and all features/ steps of the present invention. Still further, while the above embodiments are described in terms of an infusion set having a simple memory from which data is extracted and/or information can be obtained, other embodiments can utilize an infusion set that contains one or more of the determining elements of the flow regulator, as well as other elements. Indeed, some embodiments can be practiced where the flow regulator and the infusion set are a "one piece" system. In such an embodiment, by way of example and not by limitation, the one piece system could be disposable.

It is noted that while at least some of the embodiments described above are described in terms of reading a memory of the infusion set, other embodiments can be practiced where the infusion set transmits or conveys data to the flow regulator. Still other embodiments can utilize both. Thus, some embodiments of the present invention can be practiced with a regulator that receives data from a memory, where receive data includes both active reading of a memory and reception of data transmitted to the receiver.

The foregoing are but a few of the ways and techniques in which a characteristic of flow in a channel measured during manufacture (or at some other pre-use point in time) can be used to compensate for differences in actual flow of the same or different liquid at time of use. Those of ordinary skill in the relevant art will recognize other beneficial application of these techniques in improving drug and other liquid delivery. Any of the disclosed designs and techniques could be combined with other disclosed designs and techniques to further improve the accuracy of liquid delivery by infusion.

What is claimed is:

1. A device for delivering liquid via a flow channel comprising:
    a reusable component and a disposable component adapted to mate with the reusable component, wherein:
    the disposable component includes:
        a disposable component specific flow channel; and
        a memory having one or more empirical stored values indicative of at least one of an empirical flow property and an empirical geometric property of the exact same disposable component specific flow channel included in the disposable component;
    the reusable component includes:
        a controller adapted to read the one or more empirical stored values from the memory while the disposable component is mated to the reusable component, and generate a flow control signal based on the one or more empirical stored values; and
    the device includes a valve responsive to the flow control signal adapted to control flow of the liquid through the flow channel.

2. The device of claim 1, wherein the one or more empirical stored values are based on empirical data relating to the flow channel mated to the reusable component of the device.

3. The device of claim 1, wherein the flow channel is part of an infusion set and the controller is part of a flow regulator coupled to the infusion set.

4. The device of claim 3, wherein the flow regulator is adapted to be uncoupled from the infusion set.

5. The device of claim 1, wherein the empirical geometric property is indicative of a physical characteristic of the flow channel.

6. The device of claim 5, wherein the physical characteristic is selected from the group consisting of an effective cross-sectional area of the flow channel, an effective radius of the flow channel, an effective height of the flow channel, an effective width of the flow channel, and an effective diameter of the flow channel.

7. The device of claim 1, wherein the empirical flow property is indicative of a volumetric flow rate value of a fluid previously passed through the flow channel.

8. The device of claim 1, wherein the empirical flow property is indicative of a velocity of a fluid previously passed through the flow channel.

9. The device of claim 1, wherein the valve is a proportional valve.

10. The device of claim 1, wherein the valve is an on/off valve.

11. The device of claim 1, wherein the device comprises a time-of-flight sensor.

12. The device of claim 1, wherein the controller is adapted to receive data relating to a viscosity of a liquid that will be passed through the flow channel.

13. The device of claim 1, wherein the one or more stored empirical values are based on empirical data obtained during manufacture of the flow channel of the device, the one or more stored empirical values being stored in the memory during manufacture of the disposable component.

14. The device of claim 1, wherein the reusable component comprises a flow sensor adapted to measure properties of liquid flow in the flow channel.

15. The device of claim 1, wherein the reusable component comprises a flow sensor adapted to measure a velocity of liquid flow in the flow channel.

16. The device of claim 15, wherein the flow sensor is a thermal time of flight sensor.

17. The device of claim 16, wherein the thermal time of flight sensor comprises a first source adapted to introduce a thermal marker into the liquid flowing in the flow channel, a second source adapted to illuminate the liquid flowing in the flow channel and a detector adapted to measure a change in illumination from the second source that passes through the flow channel as a result of the passage of the thermal marker through the illumination from the second source.

18. The device of claim 1, wherein the flow channel has a rectangular cross-section.

19. The device of claim 1, wherein the empirical flow property is indicative of a time of flight of a fluid previously passed through the flow channel.

20. The device of claim 1, wherein the memory includes information indicative of lot number of manufacture, date of manufacture, location of manufacture, article number within the lot number of manufacture, and time of manufacture of the disposable component.

21. The device of claim 1 wherein the reusable component has been programmed to deliver the liquid according to a desired delivery regimen and the controller is adapted to control the valve to achieve the desired delivery regimen using at least one of the stored flow properties and the geometrical properties.

22. The device of claim 21, wherein the delivery regimen is a desired flow rate as a function of time or a desired volume of liquid to be delivered in a desired time interval.

23. The device of claim 1, wherein the empirical flow property is based on at least one of an empirical fluid volume previously passed through the flow channel for a given time and an empirical flow rate of a fluid previously passed through the flow channel.

24. A device for delivering liquid via a flow channel, the device comprising:
a reusable component and a disposable component adapted to mate with the reusable component, wherein:
the disposable component includes:
a disposable component specific flow channel; and
a memory having one or more empirical stored values respectively based on a product of least one of (i) an empirical volume and an empirical time, (ii) an empirical flow rate and an empirical velocity, and (iii) an empirical area and an empirical velocity, related to the exact same disposable component specific flow channel included in the disposable component; and
the reusable component includes:
a controller adapted to read the one or more empirical stored values from the memory while the disposable component is mated to the reusable component, and generate a flow control signal based on the one or more empirical stored values;
wherein the device is adapted to at least one of transfer one or more of the empirical stored values from the memory and permit reading of the one or more of the empirical stored values, and wherein the device is adapted to determine a volumetric flow rate of a liquid flowing through the flow channel based on the one or more empirical stored values.

25. The device of claim 24, wherein the device is adapted to enable the volumetric flow rate to be determined to within 1% of its actual value.

26. The device of claim 25, wherein the device is adapted to enable the volumetric flow rate to be determined to within 0.75% of its actual value.

27. The device of claim 26, wherein the device is adapted to enable the volumetric flow rate to be determined to within 0.5% of its actual value.

28. The device of claim 27, wherein the device is adapted to enable the volumetric flow rate to determined to within 0.25% of its actual value.

29. The device of claim 28, wherein the device is adapted to enable the volumetric flow rate to be determined to within 0.1% of its actual value.

30. The device of claim 24, wherein the device is adapted to enable the volumetric flow rate to be determined without utilizing actual dimensions of the interior of the flow channel.

31. The device of claim 30, wherein actual dimensions include design dimensions.

32. The device of claim 24, wherein the flow channel and memory are parts of an infusion set.

33. The device of claim 24, wherein the device is adapted to determine the volumetric flow of the liquid flowing through the flow channel based on the one or more empirical stored values when multiplied by a time of flight of the liquid.

34. The device of claim 24, wherein the empirically stored value is indicative of a time of flight of a fluid previously passed through the flow channel.

* * * * *